(12) United States Patent
Sharma et al.

(10) Patent No.: US 11,710,566 B2
(45) Date of Patent: Jul. 25, 2023

(54) ARTIFICIAL INTELLIGENCE DISPATCH IN HEALTHCARE

(71) Applicant: Siemens Healthcare GmbH, Erlangen (DE)

(72) Inventors: Puneet Sharma, Princeton Junction, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 893 days.

(21) Appl. No.: 16/434,666

(22) Filed: Jun. 7, 2019

(65) Prior Publication Data

US 2020/0388386 A1    Dec. 10, 2020

(51) Int. Cl.
*G16H 50/20* (2018.01)
*G06T 7/10* (2017.01)
(Continued)

(52) U.S. Cl.
CPC ............. *G16H 50/20* (2018.01); *G06N 20/00* (2019.01); *G06T 7/10* (2017.01); *G16H 10/60* (2018.01); *G16H 30/40* (2018.01); *A61B 6/032* (2013.01); *G06N 3/08* (2013.01); *G06T 7/0012* (2013.01); *G06T 2207/20024* (2013.01); *G06T 2207/20081* (2013.01); *G06T 2207/20112* (2013.01);
(Continued)

(58) Field of Classification Search
None
See application file for complete search history.

(56) References Cited

U.S. PATENT DOCUMENTS

2016/0066800 A1    3/2016  Sharma et al.
2017/0245821 A1    8/2017  Itu et al.
(Continued)

FOREIGN PATENT DOCUMENTS

EP        2863360 A1 *  4/2015  ........... G06K 9/6231
WO    2018015414 A1     1/2018

OTHER PUBLICATIONS

Pappa, G. L. (2021). Automatically evolving rule induction algorithms with grammar-based genetic programming (Order No. 29091877). Available from ProQuest Dissertations and Theses Professional. (2665126681). doi:http://dx.doi.org/10.22024/UniKent/01.02.86357 (Year: 2021).*
(Continued)

*Primary Examiner* — Robert A Sorey (57) ABSTRACT

Patient, user, and/or AI information are used in a multi-objective optimization to select one of a plurality of available AIs for a task. On a patient or user-specific basis, an optimal AI is selected and applied for medical imaging or other healthcare actions. The selection may be before application, avoiding costs of applying multiple AIs to obtain the best results. The optimization may be based on statistical feedback from the user for various of the available AIs, providing information not otherwise available. The optimization may be based on AI performance, AI inclusion and/or exclusion criteria, and/or pricing information. By using optimization based on various information related to the
(Continued)

patient, user, and/or available AI, the application of AI for a given user and/or patient by the computer may be improved. The computer operates better to provide more focused information through AI application.

19 Claims, 2 Drawing Sheets

(51) Int. Cl.
| | | |
|---|---|---|
| | *G16H 10/60* | (2018.01) |
| | *G16H 30/40* | (2018.01) |
| | *G06N 20/00* | (2019.01) |
| | *G16H 50/50* | (2018.01) |
| | *G16H 50/30* | (2018.01) |
| | *G16H 50/70* | (2018.01) |
| | *A61B 6/03* | (2006.01) |
| | *G06N 3/08* | (2023.01) |
| | *G06T 7/00* | (2017.01) |

(52) U.S. Cl.
CPC ............. *G16H 50/30* (2018.01); *G16H 50/50* (2018.01); *G16H 50/70* (2018.01)

(56) References Cited

U.S. PATENT DOCUMENTS

| | | | | |
|---|---|---|---|---|
| 2018/0043182 | A1* | 2/2018 | Wu | .................... A61N 5/1039 |
| 2019/0197011 | A1* | 6/2019 | Zavesky | ............ G06F 16/24578 |
| 2019/0362651 | A1* | 11/2019 | Barral | ....................... G06N 3/08 |
| 2019/0362846 | A1* | 11/2019 | Vodencarevic | ........ G16H 50/20 |
| 2020/0311938 | A1* | 10/2020 | Vincent | .................. G16H 50/20 |

OTHER PUBLICATIONS

Extended European Search Report (EESR) dated Nov. 2, 2020 in corresponding European Patent Application No. 20178302.4.
Anonymous:; "Multi-objective optimization—Wikipedia"; XP055697412; URL: https://en.wikipedia.org/w/index.php?title=Multi-objective_optimization&oldid=710626005; Mar. 18, 2016.
Anonymous:; "Dynamic programming—Wikipedia"; XP055743033; URL: https://en.wikipedia.org/w/index.php?title=Dynamic_programming&oldid=878659578; Jan. 16, 2019.
Kafiev Irshat, et al. "The Selecting of Artificial Intelligence Technology for Control of Mobile Robots" Oct. 3-4, 2018. Abstract.

* cited by examiner

ARTIFICIAL INTELLIGENCE DISPATCH IN HEALTHCARE

BACKGROUND

The present embodiments relate to use of artificial intelligence (AI) in healthcare. In medicine, AI algorithms are used for disease detection, classification, quantification, segmentation, or other purposes. Many AIs are developed and introduced by various vendors. It is difficult to judge the relative performance of each AI algorithm for the same task. Each AI is individually validated on small cohorts that may be proprietary and not available publicly, making comparison of performance difficult. For a user of the developed AIs, it is difficult to choose the optimal AI offering for a particular problem since the evidence, strength, and weakness for each such offering is not easy to compare against one another.

Healthcare providers often choose an AI vendor for all patients based on the published results presented by the vendor. The specific inclusion and/or exclusion criteria for such a published study may or may not align with the intended use-case for the vendor. As a result, it is difficult to choose which particular AI vendor solution may be optimal for a given user, let alone a given patient.

SUMMARY

By way of introduction, the preferred embodiments described below include methods, systems, instructions, and computer readable media for AI dispatch. Patient, user, and/or AI information are used in a multi-objective optimization to select one of a plurality of available AIs for a task. On a patient or user-specific basis, an optimal AI is selected and applied for medical imaging or other healthcare actions. The selection may be before application, avoiding costs of applying multiple AIs to obtain the best results. The optimization may be based on statistical feedback from the user for various of the available AIs, providing information not otherwise available. The optimization may be based on AI performance, AI inclusion and/or exclusion criteria, and/or pricing information. By using optimization based on various information related to the patient, user, and/or available AI, the application of AI for a given user and/or patient by the computer may be improved. The computer operates better to provide more focused information through AI application.

In a first aspect, a method is provided for artificial intelligence dispatch in a medical system. A medical imaging scanner scans a patient, providing a medical image representing the patient. A first artificial intelligence is selected from a group of multiple artificial intelligences. The selection is by a multi-objective optimization using the medical image, other patient data, at least one user-defined constraint, and artificial intelligence information for the multiple artificial intelligences. The selected first artificial intelligence is applied to the medical image. An output of the selected first artificial intelligence from the applying is displayed.

In one embodiment, the selection is with the multi-objective optimization being evolutionary programming, linear programming, non-linear programming, dynamic programming, or simulated annealing. The optimization may provide a pareto-optimal solution, allowing for some constraints not to be met in order to selection at least one artificial intelligence.

Various criteria may be used in the optimization. The selection may be with at least one user-defined constraint being a requirement and the artificial intelligence information being a characteristic related to the requirement. The selection may be with the at least one user-defined constraint being a goal, which is not a requirement, and the artificial intelligence information being a characteristic related to the goal. The selection may be with the at least one user-defined constraint being a clinical, operational, or financial constraint. The selection may be with the at least one user-defined constraint being a clinical indication, clinical task, cost constraint, time constraint, or output requirement. The selection may be with the artificial intelligence information being operation constraints of the artificial intelligences, performance characteristic, or pricing information.

In one embodiment, usage information regarding the artificial intelligences of the group, including the first artificial intelligence, is gathered, such as gathering statistical information about AI usage, acceptance, and/or correction. The selection by the multi-objective optimization uses the usage information. For example, the usage information is gathered as an indication of performance or constraint related information.

In other embodiments, the selection may use other patient data, such as a condition of the patient. The artificial intelligence information may be condition-related information. The selection may use the artificial intelligence information, such as cost information. By selecting based on cost, the application costs for a patient may be reduced. The application is performed after the selection.

Various outputs from the applied artificial intelligence may be displayed. For example, a segmentation, anatomy identification, disease characterization, or injury are displayed as the output.

In a second aspect, a system is provided for dispatch of machine-learned models. A memory is provided for storing machine-learned models and, for each of the machine-learned models, model performance, model inclusion criterion, model exclusion criterion, and cost. A processor is configured to dispatch, for a patient, one of the machine-learned models based on multi-objective optimization of the model performance, the model inclusion criterion, the model exclusion criterion, cost, and patient information. A display is configured to display an output of the dispatched one of the machine-learned models from application to an image of the patient.

In one embodiment, the multi-objective optimization includes model cost. The application occurs after the dispatch to reduce costs.

In other embodiments, the model performance, model inclusion criterion, or model exclusion criterion is based on statistical usage feedback from previous dispatches of the machine-learned models. The model inclusion criterion and/or the model exclusion criterion may include soft constraints in the multi-objective optimization. The multi-objective optimization may also be of user inclusion criterion and user exclusion criterion.

In a third aspect, a system is provided for dispatch of artificial intelligence. A memory is provided for storing artificial intelligence offerings and task-related information for each of the artificial intelligence offerings. A processor is configured to dispatch, for a patient, one of the artificial intelligence offerings identified by multi-objective optimization of the task-related information and patient-related information. A display is configured to display an output of the dispatched one of the artificial intelligence offerings from application to an image of the patient.

In other embodiments, the task-related information is operational, financial, and/or clinical information, and the patient-related information is the image, patient condition data, and/or one or more constraints.

The present invention is defined by the following claims, and nothing in this section should be taken as a limitation on those claims. Parts of one type of claim (e.g., method or system) may be used in other types of claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

An AI dispatcher service automatically identifies an optimal (e.g., the most optimal) AI offering from among the available options. The AI offering is identified in a patient-specific, user-specific, and/or task-specific manner. The pros and cons of various AI services, such as their statistical performance, inclusion and exclusion criterion and cost, are holistically modeled as a multi-objective optimization problem with constraints. Rather than failing to account for the performance characteristics of various AI services in choosing the appropriate solution and/or vendor for patient data of a given patient, the patient data may be used in a dynamic or real-time selection of AI. Rather than choosing the AI service with the lowest cost or the highest advertised performance, optimization based on multiple of user, patient, and/or AI criteria may result in a better balance between multiple objectives for a given (e.g., patient-specific) application. Dispatching AI may avoid poor performance by a computer of the medical task performed by AI, particularly for patient and/or institution specific application.

Figure 1:
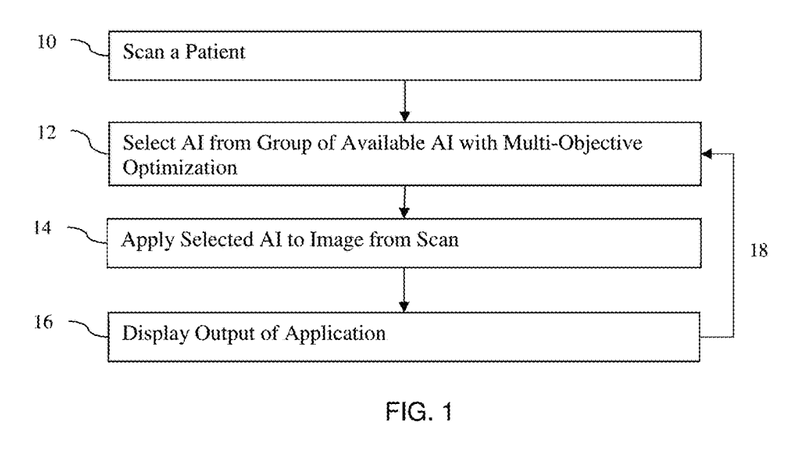
FIG. 1 is one embodiment of a method for AI dispatch in a medical system.
Figure 2:
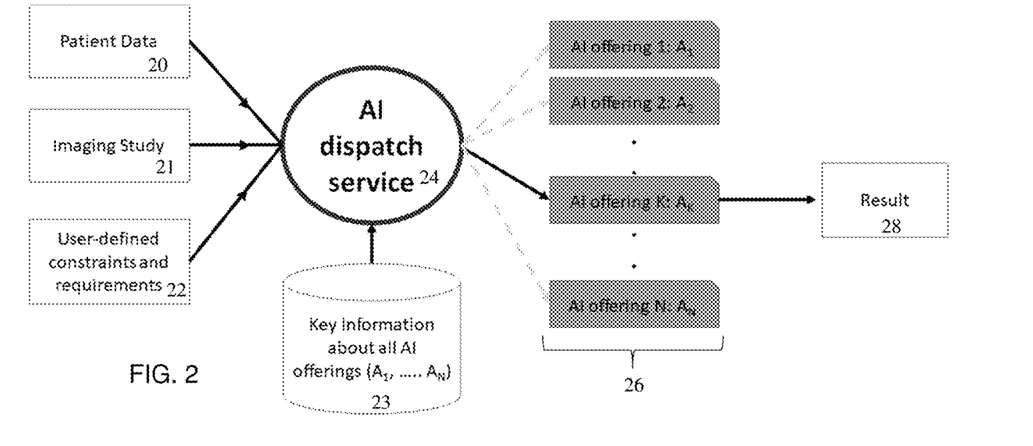
FIG. 2 illustrates a model of dispatch of AI offerings for a patient and user.

FIG. 1 shows one embodiment of a method for artificial intelligence dispatch in a medical system. An AI is selected from a group of AIs given specific patient and/or user information. A multi-objective optimization is performed to allow for use of multiple criteria in the selection. FIG. 2 illustrates a model of the dispatch of the method of FIG. 1.

Figure 3:
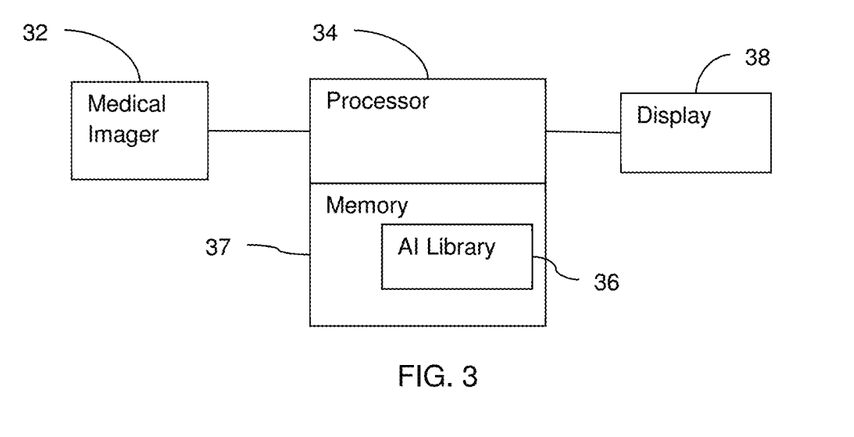
FIG. 3 is a block diagram of one embodiment of a system for machine-learned model dispatch.

The method is implemented by the system of FIG. 3 or another system. For example, the method is implemented in a medical system. The medical system has access to medical information, such as patient information, so may be a workstation in a hospital, a medical scanner, or a physician's computer. The medical system is a computer, server, medical imager, or other processor. A medical imager scans in act 10. An image or other processor (e.g., processor of the medical imager, other processor, server, or computer) selects in act 12. A same or different device (e.g., server, computer or processor) applies the selected AI in act 14 and/or provides feedback in act 18. A display device displays in act 16. Different devices may be used for one or more of the acts.

Additional, different, or fewer acts may be provided. For example, the scan of act 10 is not provided, such as where non-imaging data is used without imaging data. As another example, the output is to a memory (e.g., medical record) and/or computer network rather than a display in act 16. Act 18 may not be provided in other embodiments.

The acts are performed in the order shown (e.g., top to bottom or numerical) or other orders. For example, act 10 may be applied after act 12, such as where the image is not used in the selection but is used in the application.

In act 10, a medical imaging scanner scans a patient. The medical imaging scanner is any medical imager, such as a computed tomography (CT), magnetic resonance (MR), C-arm, ultrasound, x-ray, photoacoustic tomography, optical camera, depth camera, diffuse optical imaging, magnetic particle imaging, optical coherence tomography, nuclear medicine (e.g., single photon emission computed tomography or positron emission tomography), or other medical scanner for scanning the interior and/or exterior of a patient.

The patient is scanned along a plane or in a volume. Energy, such as x-rays, electromagnetic pulses, acoustic, or other, may be transmitted into the patient. The energy as passed through the patient is detected, and/or a response to the energy is received or detected from the patient. Alternatively, the scan measures emissions from within the patient. The detected response, energy, or emissions are scan data.

The scan data may be processed as part of the scan. For example, reconstruction is applied. The reconstruction may determine response of the patient by locations within the patient, such as for voxels or pixels in a volume or plane of the patient. For MR, k-space data is reconstructed with a Fourier transform. For CT, projection images from different directions relative to the patient are reconstructed by computed tomography. For nuclear medicine, detected emissions along lines of response are reconstructed by tomography.

The scan data is used to generate a medical image representing the patient. Format conversion, filtering, reconstruction, rendering, mapping, and/or another process are applied to convert the scan data into a medical image. The medical image may be scan data prior to processing. The medical image represents a spatial distribution of measurements from the patient. The spatial distribution may be in one, two, or three dimensions. The medical image may be a grayscale or color image displayed on or for display on a display screen or may be scalar values prior to mapping to display values.

The model of FIG. 2 uses input of an imaging study 21. The medical image with or without other information linked to the medical image (e.g., scan settings such as resolution or scale of the image) are obtained.

Non-scan data may be obtained. Data from other sensors, lab results, history, findings, or other information are obtained by receipt or look-up. For example, a clinical task for the patient is identified from a medical record, such as a physician's order. As another example, a clinical indication is identified from a medical report or billing database. Any clinical indication, such as a diagnosis, prognosis, symptoms, risk factor (e.g., smoker or not), and/or disease identification may be obtained. The medical image with or without other data is obtained. Alternatively, patient data without imaging or scan data is obtained.

The model of FIG. 2 uses input of patient data 20. The patient data 20 is non-imaging data for the patient.

The patient data and/or medical image may be obtained from memory, such as a computerized patient record or a picture archiving and communications system. The data may be obtained by entry on a user interface. The patient data may be obtained from multiple sources, such as by mining a medical record and/or billing database. The data may be obtained from the medical scanner. Other data, such as user-defined constraints 22 of FIG. 2 and/or the AI information 23 of FIG. 2, are obtained from a memory, user input, and/or other source.

In act 12 of FIG. 1, a processor selects an artificial intelligence from a group of multiple artificial intelligences. For a given task or application (e.g., segmentation of a lesion in the liver), there are multiple machine-learned models that may be applied. Any variety of machine-learned models may be available. Different training data, different types of machine learning, different architectures, and/or any other differences in machine learning may result in different AIs for the same task. Machine-learned models for one task may be useable for another task, making the number of available artificial intelligences larger.

The AIs are from one or multiple vendors. For example, one designer or creator of AI for a given task may provide only one, two, or more AIs for the same task. Different vendors or the same vendor provide all of the available AIs.

In the example of FIG. 2, N AI offerings (AI offering 1 through N) 26 from one or more vendors are shown. N is an integer greater than 1. Each of these algorithms (i.e., machine-learned models) are approved for medical use from a regulatory point of view for the task. The AI dispatch service 24 selects one of the AI offerings 26 for the selection of act 12 of FIG. 1. The service 24 is a service of the processor or is a service provided by a different entity than an employer of the user or treating medical institution of the patient (i.e., service of the other entity to a clinical user). Alternatively, the service is provided by the user or treating institution as a service to the patient.

Some example tasks include AI offerings 26 for detection and/or characterization (e.g., stage) of cancer (lesions) in CT, MRI, mammography, and/or ultrasound exams. Other examples are AI offerings are for detection and/or characterization of bleeding or trauma in medical images. AI offerings may be provided for detection and/or characterization of plaques and stenosis in medical images. AI offerings may be provided for detection of bleeding or fracture in CT scans.

The selection of act 12 uses a multi-objective optimization. More than one criterion is used in the selection. The processor selects by performing the multi-objective optimization. With reference to FIG. 2, the AI dispatch service 24 solves the multi-objective optimization problem and chooses one of the multiple AI offerings 26 for the task and data at hand. The AI dispatcher service 24 decides upon the optimal AI offering 26 depending on a variety of constraints and/or user requirements, such as clinical, operational (e.g., length of time to obtain results and data privacy risk), financial (e.g., cost of use of AI), and/or other constraint or requirement.

Different multi-objective optimizations may be used. Evolutionary programming, linear programming, non-linear programming, dynamic programming, or simulated annealing may be used to solve for an objective. The multi-objective function is implemented as an analytic process solving for an optimal solution with an objective function having multiple considerations. In an alternative embodiment, the multi-objective function is implemented as a machine-learned model. The inputs are provided to a model that was machine trained to provide the output selection given the inputs for multiple considerations.

The objective ranks, weights, and/or penalizes different considerations in the optimization. A default objective may be used. Alternatively, a user or entity controlling use may set the objective function. By setting the objective function, the prioritization of minimization or maximization of considerations is established. The optimization is controlled to make decisions or optimize for one or more considerations more strongly than for other considerations in the multiple objectives.

By using a multi-objective optimization for selection of AI, a pareto-optimal solution may be provided. The pareto-optimal solution allows for some constraints not to be met, so may provide an AI where no AI meets all constraints. In other embodiments, the optimization requires meeting of all constraints, such as all hard constraints or requirements. Techniques such as dynamic programming or evolutionary algorithms may be used to solve for an optimal or pareto-optimal solution to the given problem.

The different machine-learned models may have different constraints (e.g., operate on different types of data or use different input data), cost, performance, and/or operational limitations (e.g., speed of providing results). Different ones of these characteristics may be available, such as provided by the vendor or in a publication. Other characteristics may be determined by testing or from another source. The characteristics may be different for different patient information and/or user settings or constraints. The characteristics may limit applicability, such as requiring data at a given resolution or only working with one type of medical imaging (e.g., CT or MR).

A constraint on the optimization may be a hard constraint or a soft constraint. A hard constraint is a requirement. The selected AI must meet the constraint, such as a having to meet a performance constraint. A soft constraint is a goal that may not be met. The optimization seeks to meet or exceed the goal, but the selected AI may not meet or exceed the goal. The AI dispatcher service 24 is based on solving a multi-objective optimization problem with multiple hard and soft constraints.

Constraints, variables in the objective being minimized or maximized, and/or other variables form the multi-objective optimization function. This information relates to the user (e.g., user-defined constraint), patient (e.g., medical image and/or other patient data), and/or AIs and is input as considerations in the optimization to select one or a subset of AIs from the available AIs for a task. The user and patient information are the same for a given optimization while the AI information may be the same or different for different AI offerings for a given task.

The optimization may balance or compare information. Patient and/or user information may be balanced or compared in the optimization to AI information. A user-defined and/or patient requirement is used in the selection where the AI information includes a characteristic related to the requirement. A user-defined and/or patient goal is used in the selection where the AI information includes a characteristic related to the goal. The optimization compares the information to select a more optimal AI given requirements and/or goals. For example, the cost is limited by the patient or the user as a goal or soft constraint. The AI information includes costs to apply AI so that the optimization selects an AI offering that satisfies hard constraints while minimizing the cost. As another example, the condition of the patient (e.g., indicators of risk applicable to the patient, such as cancer diagnosis and family history of cancer) is compared to performance of the AI for patients with the condition. The minimization of the cost may be balanced with optimization of other variables including other requirements and/or goals, such as optimizing for both cost and condition matching.

For patient-specific optimization, the AI dispatch service 24 takes as input the medical image(s) 21 for a specific patient and/or other patient data 20 for that patient. This other patient data may be the patient's condition (e.g., diagnosis, symptoms, clinical indicators, family history, test results, and/or prognosis). In one embodiment, the other patient data is a condition of the patient. The patient data and images are obtained from a computerized patient medical record, manual input, and/or access to one or more databases. Information from the image, such as slice thickness, resolution, signal-to-noise ratio, or features from the image may be useful in conjunction with the AI information from each vendor. Derived information from the image (e.g. filed-of-view, what are the specific organs in the field of view etc.) may be useful to help select the best AI offering.

For user-specific optimization, the AI dispatch service 24 takes as input constraints, such as requirements or goals, for the user. The user, such as a clinical entity or medical professional, may define one or more constraints as user preferences or requirements. The definition may be in general, for the task, or for the patient. In alternative embodiments, default constraints are used as the user-defined constraints. Other information from the user may be used in the optimization, such as in the objective function or as a variable other than a constraint.

The user-defined constraint may be a clinical, operational, or financial constraint. The operational constraint may be a time constraint, such as an amount of time to return an output. The AI optimization has a goal or requirement based on the processing speed of the AIs. Other operational constraints may be provided, such as whether the vendor of the AI has an agreement with the clinical entity or a level of service by the vendor.

The financial constraint may be a cost of application of the AI. Different AI offerings may have different costs, such as where the AIs are provided by third party vendors. The user-defined constraint may be a cost to the user or a cost added by the user. Other financial constraints include cost of physician review, such as where results from one AI may be more easily interpreted than results from a different AI, discounts (e.g., by number of uses by the clinical user), and/or liability risk for false positives. The financial constraint may be a goal or a requirement.

The clinical constraint may be information related to a clinical indication, clinical task, or output. Any clinical indication may be used, such as an indication of the reason for an examination. The user-defined constraint for the clinical indication may provide user-based guidelines, treatment norms, equipment availability, or other indication information for the user. The clinical task for the user-defined information may be anatomy of interest and type of AI process to be used. Different users may desire different types of AI processes for different anatomy. The output may be an output requirement or goal for the AI. The user may establish information to be output for clinical diagnosis, prognosis, or treatment planning. Different users may desire different outputs.

Referring to FIG. 2, the AI dispatch service 24 receives AI information 23 about the AI offerings 26. This AI information 23 provides AI vendor and/or AI-specific information, such as constraints, to be used in the optimization.

The AI information 23 may be operation constraints, performance characteristic, or pricing information of the AIs. The pricing information may be the cost of using the AI, such as how much the vendor charges per patient case. The cost from the AI vendor may be compared to the cost constraint of the user or patient. Other pricing information may be used, such as any discounts offered.

The operation constraints may be requirements or goals for input data, such as required patient information. For example, the image of the patient may be limited to a certain modality (e.g., MR or CT), resolution, field of view, or scale. The operation constraint may be an amount of time needed to provide output and/or the output provided. The operation constraint may be for which clinical tasks and/or indications the AI is approved or operable. For example, an AI for lung nodule detection in CT images from one vendor may only be available for solid and sub-solid nodules, while a similar offering from another vendor may work for all nodules. If the AI is not trained for detecting a particular type of lung nodule, then that case is considered an "exclusion" criterion for that AI in the optimization. Often time, the AIs have strict exclusion criterion when it comes to technical factors concerning imaging. For example, images with slice thickness >3 mm will not be processed, or images should at least have 0.5 mm in-plane resolution.

The performance characteristic may be information indicating reliability or risk in application by the AI. For example, the performance characteristics used in optimization may include sensitivity, specificity, positive predictive value, negative predictive value, accuracy, receiver operating characteristic (ROC) curve, area under the ROC curve, or other measure of performance of the AI. The performance may be different for different applications, such as a different ROC for identifying one type of nodule than for another type of nodule. The performance may be normalized, such as testing different AI offerings on a same set of test data with known results. Alternatively, the performance may be for each AI without normalization (e.g., using published performance information from the vendor for their AI offering).

The AI information 23 is obtained from published results. The vendor or creator of the AI offering may publish an article or fact sheet for the AI offering, from which the AI information is extracted. The vendor may provide the AI information, such as providing as part of an agreement for use or access. The AI information may be from FDA approval and/or submission. Other sources may be provided.

In one embodiment, natural language processing (NLP) techniques are used to extract key information from clinical publication. Clinical trials for the AI may have structured formats where such information is tabulated, so the AI information may be extracted automatically using this structure. A published meta-analysis where the investigators tabulate and compare various AI offerings may be used to extract the AI information.

In another embodiment, usage information is gathered in act 18 of FIG. 1 based on application and display of previous performances of acts 14 and 16. As a given user or multiple different users select, use output, and/or correct output of different AI offerings for different patients, this usage data is gathered. Log files, user-interface tracking, or other background process may be used to gather the usage of the different AIs. The AI information 23 about a particular AI offering 26 may be derived by a program or platform for AI selection by usage over time (i.e. information collected from the usage of a AI offerings). Where several offering for the same clinical indication or task are available from different vendors, such as in a radiology application or platform, the comparative usage may be tracked and used to set the AI information.

The usage information indicates operation constraints, performance characteristic, and/or pricing information. For example, the accuracy is indicated by whether an output is changed by the user. As another example, the operation of selected AIs is tracked, providing operation constraints (e.g., time to provide results).

In one example, the explicit or implicit user feedback is tracked over time. The acceptance or rejection of the results and/or findings of the AI algorithm is tracked. The acceptance or rejection may be provided by whether the output is edited or accepted as is. Trends of a particular user may be tracked in terms of the pay-per-case. If the user utilizes the AI offering more and more, then this information indicates that the accuracy and/or other performance of that particular AI is high. The kind of exams that a user typically routes one of these AIs may be tracked. For example, if only low-dose CT scans are routed to a particular AI offering, and a regular dose CT exam is rarely routed to the particular AI offering, sub-group performance of that AI offering may be set where performance is relatively low for regular dose and relatively high for low-dose.

This usage information is used as an indication of AI information (e.g., performance or constraint related information). The multi-objective optimization uses the usage information, such as setting a constraint or variable based on AI information that is derived from the usage. The selection of the AI is a function of the previous usage by a given user or by users in general of the selected and/or other AI offerings.

In act 14, the processor applies the selected AI. The AI uses input data to generate an output. The input data may be the same or different than the patient information (e.g., imaging study 21 and other patient data 20) used to select the AI.

This application occurs after selection. Rather than pay to apply different AIs to determine which provides the desired result for the patient, the selected AI or selected sub-set of AIs are applied.

In one embodiment, one or more images of the patient are input to the selected AI. Alternatively, features derived from the image or images of the patient are input. Other data may be input, such as other patient data (e.g., test results, family history, and/or patient characteristics).

In response to input of the input feature vector, the AI outputs information. Classification, detection, segmentation, or other characterization is output. For example, the AI outputs a location and characterization of a lesion, bleeding, stenosis, plaque, and/or fracture represented in the input patient medical image.

In act 16, the output of the application of the selected AI is displayed. The processor generates an image, formatted for a display screen. The display screen displays the image.

The image includes the output of the AI or information derived from the output of the AI. For example, an annotation, marker, segmentation, or highlighting is displayed. The anatomy identification, disease characterization, injury, or other information from the AI is output on the image using the annotation, marker, segmentation, or highlighting. The AI may generate an image as an overlay or for display without overlay. A segmentation by the AI may be used to calculate a quantity, such as a volume or area. The volume or area may be output.

The output from the AI or information derived from the output of the AI may be displayed with or without the medical image used as input. For example, an image of anatomy (e.g., CT or MR) is generated where an annotation, marker, or highlighting from the AI output is included on the image.

FIG. 3 shows a block diagram of one embodiment of a system for dispatch of machine-learned models or AI. When there are multiple available machine-learned models to provide the same information or for a same task for a patient, the system selects the model to be applied based on multi-objective optimization using patient and/or user-specific information. The system implements the model of FIG. 2, the method of FIG. 1, or a different model or method.

The system includes one or more medical imagers 32, a processor 34, a memory 37 (e.g., a medical records database), and a display 38. Additional, different, or fewer components may be provided. For example, a user interface or input device is provided on the medical imager 32 and/or for the processor 34. In another example, a network or network connection is provided, such as for networking different components (e.g., medical imager 32 with the processor 34 and/or the processor 34 with the memory 37).

The memory 37, processor 34, and/or display 38 are part of a server, workstation, or computer. In one embodiment, the memory 37, processor 34, and/or display 38 are part of the medical imager 32. The memory 37 may be part of a separate computer from the processor 34, such as being in a cloud hosted electronic health record or electronic medical records system.

The medical imager 32 is a magnetic resonance (MR), computed tomography (CT), x-ray, ultrasound, nuclear medicine (e.g., positron emission tomography or single photon computed tomography), or another medical scanner. In other embodiments, the medical imager 32 is a multi-modality device, such as a combination of nuclear medicine and x-ray or CT. In yet other embodiments, invasive, other non-invasive, or minimally invasive imaging systems are used.

The medical imager 32 is configured to scan a patient. The same imager 32 may be used to scan different patients at different times. Other imagers 32 may be used to scan other patients. The medical imager 32 is configured to output scan data to the processor 34. The scan data is data resulting from the scan at any stage of processing. For example, data without reconstruction is provided. For CT, the data may be detector measurements for a plurality of projections without reconstruction into values for specific spatial locations. For MR, the data may be k-space data prior to Fourier transform to determine values for specific spatial locations. For nuclear imaging, the data may be line-of-response values prior to tomography to assign specific spatial locations. As another example, data after reconstruction is provided. Filtering, detection, scan conversion, and/or other image processing may or may not be applied to the data for communication to the processor 34. The medical imager 32 provides image data (e.g., scan data) as data resulting from scanning with any amount of processing towards generating an image on the display 38. The image data may be formatted for display, such as RGB values, or may be in a scan format (e.g., scalar values).

The memory 37 is a random-access memory, system memory, cache memory, hard drive, optical media, magnetic media, flash drive, buffer, database, combinations thereof, or other now known or later developed memory device for storing patient information, AI information, user information, and/or a library 36 of available machine-learned models. The memory 37 is part of the computer associated with the processor 34 or the medical imager 32 or is a separate or remote database for access over a computer network.

The machine-learned models of the library 36 are for different or the same clinical tasks. More than one machine-learned model may be available for a given task and type of imaging. This library 36 of AI offerings include multiple options to be applied or used for a given patient.

The memory 37 stores task-related information for each of the artificial intelligence offerings. For the task or tasks of each machine-learned model, AI information is stored. For example, operational, financial, and/or clinical information for each AI offering is stored. The model performance, model inclusion criterion, model exclusion criterion, and cost may be stored for each of the machine-learned models.

The memory 37 may store patient information (e.g., medical image data from the medical imager 32 or another imager and/or other patient data). The memory 37 may include a computerized medical record for the patient. Some or all of the patient information may be provided by transfer or access to a device other than the memory 37.

The memory 37 may store user information (e.g., constraints). The inclusion and/or exclusion criteria for the user are stored as hard or soft constraints. Constraint values from a user interface or file are stored.

The memory 37 or other memory is alternatively or additionally a non-transitory computer readable storage medium storing data representing instructions executable by the programmed processor 34 and/or medical imager 32. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, tensor processing unit (TPU), neural processing unit, AI accelerator, or system.

The processor 34 is a general processor, control processor, digital signal processor, application specific integrated circuit, field programmable gate array, or other hardware processor for selecting a machine-learned model based on multi-objective optimization and/or application of the selected machine-learned model. In one embodiment, the processor 34 is part of a computer, workstation, server, or other device configured to select and apply a machine-learned model. The processor 34 may be a network of computing devices, such as multiple computers or servers. The processor 34 is configured by software, hardware, and/or firmware.

The processor 34 is configured to dispatch one of the artificial intelligence offerings identified by multi-objective optimization. The multi-objective optimization uses task-related information and patient-related information. Task-related information may be user and/or AI-specific information for the task for the patient. For example, for a patient, one of the machine-learned models of the library 36 is dispatched (e.g., selected) based on multi-objective optimization of the model performance, the model inclusion criterion, the model exclusion criterion, cost, and patient information. Model inclusion criterion and/or the model exclusion criteria may be soft or hard constraints in the multi-objective optimization. The inclusion and/or exclusion criteria may be for the clinical user and/or for the AIs of the library 36.

Two or more considerations are used in the objective function of the optimization. For example, cost and one or more constraints are used to select the machine-learned model. By including both patient information and AI information in the objectives, the machine-learned model optimally suited for the given patient at the time of selection is dispatched. For example, the image or characteristics of the image (e.g., type such as CT or MR, resolution, scale, and/or field of view) of the patient, patient condition data (e.g., other data for the patient or non-image data), and constraints for the available machine-learned models for the task are used in optimization to select the machine-learned model to use for the patient. User, patient, and/or AI constraints or other information may be used in the optimization.

In one embodiment, the processor 34 is configured to dispatch based on statistical usage feedback from previous dispatches of one or more of the machine-learned models in the library 36. The model performance, model inclusion criterion, model exclusion criterion, or other AI information is based on statistical usage feedback from previous dispatches of the machine-learned models. A given statistic or combinations of statistics are used to set a value for one or more variables used in the optimization.

The processor 34 or a different processor is configured to apply the dispatched machine-learned model. The machine-learned model is applied to data from the patient, resulting in generation of an output to assist in diagnosis, prognosis, and/or treatment planning for the patient. Due to the optimization, the output from the application is more likely to help for diagnosis, prognosis, and/or treatment planning.

The display 38 is a monitor, LCD, projector, plasma display, CRT, printer, or other now known or later developed device for displaying an output of the dispatched machine-learned model or AI offering. By applying the machine-learned model to patient information such as a medical image of the patient, an output is generated. The display 38 displays an image representing the output or information derived from the output.

The display 38 receives the output from the processor 34, medical imaging scanner 32, or memory 37. The processor 34 formats the data for display (e.g., mapping to RGB values) and stores the image in a buffer, configuring the display 38. The display 38 uses the image in the buffer to generate an image for viewing. The image includes graphics, alphanumeric text, anatomical scan, and/or other information representing the output or information from the output. The display 38 is at the medical imager 32, the processor 34, a physician's computer, or another location.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for artificial intelligence dispatch in a medical system, the method comprising:

scanning, by a medical imaging scanner, a patient, the scanning providing a medical image representing the patient;

selecting, by a processor of the medical system, a first artificial intelligence from a group of multiple artificial intelligences, the multiple artificial intelligences of the group being for a same task, the selecting being by a multi-objective optimization as a machine-learned model solving for an optimal solution with an objective function, the machine-learned model having been trained to output a selection given inputs, the objective function having variables in the solving as the inputs, the variables comprising the medical image, other patient data, at least one user-defined constraint, and artificial intelligence information for the multiple artificial intelligences, different ones of the variables of the medical image, other patient data, at least one user-defined constraint, and artificial intelligence information for the multiple artificial intelligences prioritized differently from each other in the objective function, the objective function configured for the variable of the at least one use-defined constraint as either of a requirement or a goal in the solving for the optimal solution, the other patient data comprising a condition of the patient;

applying, by the processor of the medical system, the selected first artificial intelligence to the medical image; and displaying an output of the selected first artificial intelligence from the applying.

2. The method of claim 1 wherein selecting comprises selecting with the multi-objective optimization comprising evolutionary programming, linear programming, non-linear programming, dynamic programming, or simulated annealing.

3. The method of claim 1 wherein selecting comprises selecting with the multi-objected optimization providing a pareto-optimal solution.

4. The method of claim 1 wherein selecting comprises selecting with the at least one user-defined constraint being the requirement and the artificial intelligence information comprising a characteristic related to the requirement.

5. The method of claim 1 wherein selecting comprises selecting with the at least one user-defined constraint being the goal, which is not a requirement, and the artificial intelligence information comprising a characteristic related to the goal.

6. The method of claim 1 wherein selecting comprises selecting with the at least one user-defined constraint being a clinical, operational, or financial constraint.

7. The method of claim 1 wherein selecting comprises selecting with the at least one user-defined constraint being a clinical indication, clinical task, cost constraint, time constraint, or output requirement.

8. The method of claim 1 wherein selecting comprises selecting with the artificial intelligence information comprising operation constraints of the artificial intelligences, performance characteristic, or pricing information.

9. The method of claim 8 further comprising gathering usage information regarding the artificial intelligences of the group, including the first artificial intelligence, and wherein selecting comprises selecting by the multi-objective optimization using the usage information.

10. The method of claim 9 wherein gathering the usage information comprises gathering the usage information as an indication of performance or constraint related information.

11. The method of claim 1 wherein the artificial intelligence information comprises condition-related information.

12. The method of claim 1 wherein selecting comprises selecting with the artificial intelligence information comprising cost information and wherein applying occurs after the selecting.

13. The method of claim 1 wherein displaying comprises displaying a segmentation, anatomy identification, disease characterization, or injury as the output.

14. The method of claim 1 wherein selecting comprises selecting the first artificial intelligence from the group of multiple artificial intelligences, the multiple artificial intelligences of the group being for a same task, the same task being detection or characterization of the medical image and being for a same organ.

15. A system for dispatch of machine-learned models, the system comprising:

a memory for storing machine-learned models and, for each of the machine-learned models, model performance, model inclusion criterion, model exclusion criterion, and cost;

a processor configured to dispatch, for a patient, one of the machine-learned models resulting from an optimal solution of an objective function in a multi-objective optimization with inputs of the model performance, the model inclusion criterion, the model exclusion criterion, cost, and patient information to the objective function, the dispatch using the multi-objective function implemented as model having been machine trained to receive the inputs and output a selection, different ones of the inputs prioritized differently in the objective function, the objective function configured for the model exclusion criterion or the model inclusion criterion as a user selection from requirement or goal options, both the requirement and goal options being available to the user; and a display configured to display an output of the dispatched one of the machine-learned models from application to an image of the patient.

16. The system of claim 15 wherein the multi-objective optimization includes model cost, and wherein the application occurs after the dispatch.

17. The system of claim 15 wherein the model performance, model inclusion criterion, or model exclusion criterion is based on statistical usage feedback from previous dispatches of the machine-learned models.

18. The system of claim 15 wherein the model inclusion criterion and/or the model exclusion criterion comprise soft constraints in the multi-objective optimization as the goal option.

19. The system of claim 15 wherein the multi-objective optimization is also of user inclusion criterion and user exclusion criterion.

* * * * *